(12) United States Patent
Lin

(10) Patent No.: US 8,323,225 B2
(45) Date of Patent: Dec. 4, 2012

(54) TOE EXTROVERSION CORRECTION DEVICE

(75) Inventor: Wei-Cheng Lin, Yilan County (TW)

(73) Assignee: Dr. Foot Technology Co., Ltd., Yilan County (TW)

( * ) Notice: Subject to any disclaimer, the term of this patent is extended or adjusted under 35 U.S.C. 154(b) by 296 days.

(21) Appl. No.: 12/845,139

(22) Filed: Jul. 28, 2010

(65) Prior Publication Data

US 2011/0046531 A1 Feb. 24, 2011

(30) Foreign Application Priority Data

Aug. 18, 2009 (TW) .............................. 98215211 U

(51) Int. Cl.
*A61F 5/00* (2006.01)
*A43B 7/26* (2006.01)
(52) U.S. Cl. ............................................. 602/30; 36/94
(58) Field of Classification Search ................... 602/1, 5, 602/23, 30, 31; 36/94, 11.5, 95, 140, 141, 36/138; 128/889, 890, 888; D2/916, 919; D28/61
See application file for complete search history.

(56) References Cited

U.S. PATENT DOCUMENTS

| 2,596,038 | A | * | 5/1952 | Mayer | 602/30 |
| 3,049,120 | A | * | 8/1962 | Edith | 602/30 |
| 2008/0301977 | A1 | * | 12/2008 | Roberts et al. | 36/94 |

* cited by examiner

*Primary Examiner* — Loan Thanh
*Assistant Examiner* — Tarla Patel
(74) *Attorney, Agent, or Firm* — WPAT, P.C.; Anthony King

(57) ABSTRACT

A toe extroversion correction device includes a support portion integrally formed and made of a soft material, a first toe sheath portion disposed on a lateral side of the support portion, a second toe sheath portion disposed on another lateral side of the support portion, and a protection pad portion protruded from a lateral side of the first toe sheath portion, such that the first toe sheath portion is sheathed on big toe, and the second toe sheath portion is sheathed on the second toe, and the support portion is clipped between the big toe and the second toe to produce an action force to push away the big toe, and the protection pad portion can be attached onto an internal side of a first toe joint of the big toe to prevent the protruding first toe joint of the extroverted big toe from being rubbed with a shoe.

1 Claim, 3 Drawing Sheets a-a'

TOE EXTROVERSION CORRECTION DEVICE

CROSS-REFERENCE TO RELATED APPLICATION

This non-provisional application claims priority under 35 U.S.C. §119(a) on Patent Application No(s).098215211 filed in Taiwan, R.O.C. on Aug. 18, 2009, the entire contents of which are hereby incorporated by reference.

FIELD OF THE INVENTION

The present invention relates to a toe extroversion correction device, in particular to a toe extroversion correction device sheathed on a big toe and a second toe for resuming an extroverted big toe into its original shape and attached onto an internal side of a first toe joint of the big toe for protecting the first toe joint of the big toe.

BACKGROUND OF THE INVENTION

A common toe extroversion refers to a condition that a big toe leans towards a second toe, and a first toe joint of the big toe is deformed and protruded, and such condition is generally related to a congenital genetic factor or an acquired abnormal force applied to a foot, particularly for a person who wears high heels, pointed shoes, or too-narrow shoes for long time, such that the wearer's body weight concentrates at the front end of the foot during walking and destroys the function of the original three foot arcs, and the big toe and other toes may be deformed gradually due to the wearer's body weight, or the big toe and other toes may be rubbed and compressed to affect the stretch and movement of the toes. After a long time, the big toe may be extroverted and the first toe joint may be deformed and protruded, and the internal side of the deformed and protruded first toe joint is usually rubbed with the shoe to produce calluses and corns. For serious cases, surgical operations may be required.

However, general toe extroversions can be corrected by wearing a big toe extroversion correction device to rebuild toe bones. With reference to FIG. 1 for a conventional big toe extroversion correction device 10, the big toe extroversion correction device 10 comprises a cylindrical body made of a soft material, and concave clamp portions 101 disposed on the cylindrical body, such that the device 10 can be installed between the big toe and the second toe to spread the extroverted big toe. However, the condition of the big toe extroversion cannot be corrected or recovered in a short time, and the deformed protruding the toe joint is still rubbed frequently during the correction period. Therefore, it is an important subject for the present invention to protect the protruding portion and develop a toe extroversion correction device in order to correct the extroverted big toe, while protecting the deformed protruding position of the first toe joint and the protruding portion of the first toe joint.

SUMMARY OF THE INVENTION

In view of the foregoing shortcomings of the prior art, the inventor of the present invention based on years of experience in the related industry to conduct extensive researches and experiments, and finally developed a toe extroversion correction device, in hope of correcting a toe extroversion condition while protecting the protruding deformed position of a first toe joint and preventing it from being rubbed.

It is a primary objective of the present invention to provide a toe extroversion correction device integrally formed, and comprising a structural design of a protection pad portion, such that the toe extroversion correction device can be worn onto a big toe and a second toe, and the protection pad portion can be attached onto a protruding deformed position of a first toe joint to achieve the effects of correcting a toe extroversion and protecting an internal side of the first toe joint.

To achieve the foregoing objective, the present invention provides a toe extroversion correction device comprising: a support portion integrally formed and made of a soft material, a first toe sheath portion disposed on a lateral side of the support portion, a second toe sheath portion disposed on another lateral side of the support portion, and a protection pad portion protruded from a lateral side of the first toe sheath portion.

In the toe extroversion correction device of the present invention, the first toe sheath portion is sheathed on a big toe, and the second toe sheath portion is sheathed on a second toe, such that the support portion can be clipped between the big toe and the second toe to produce an action force to push away the big toe, and the protection pad portion can be attached onto an internal side of a first toe joint of the big toe to prevent the protruding first toe joint of the extroverted big toe from being rubbed with a shoe.

DESCRIPTION OF THE PREFERRED EMBODIMENTS

The objects, characteristics and effects of the present invention will become apparent with the detailed description of the preferred embodiments and the illustration of related drawings as follows.

Figure 1:
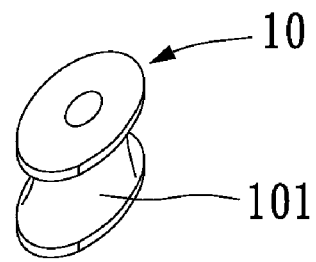
FIG. 1 is a perspective view of a conventional big toe extroversion correction device.
Figure 2:
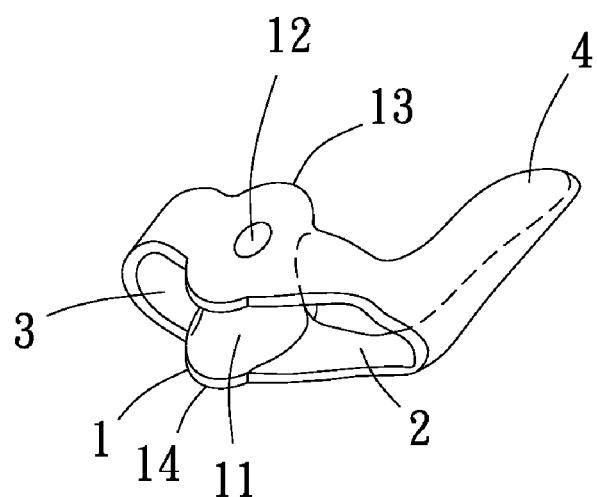
FIG. 2 is a perspective view of a preferred embodiment of the present invention.

With reference to FIG. 2 for a toe extroversion correction device in accordance with a preferred embodiment of the present invention, the toe extroversion correction device comprises a support portion 1 integrally formed with a soft material such as silicone, rubber or a foaming material, a first toe sheath portion 2 disposed on a lateral side of the support portion 1, a second toe sheath portion 3 disposed on another lateral side of the support portion 1, and a protection pad portion 4 protruded from a lateral side of the first toe sheath portion 1 and matched with an internal side of a first toe joint of the big toe. The support portion 1 is a cylindrical body including a concave clamp portion 11 enclosed around a middle section of the cylindrical body, a through hole 12 formed at the center of the cylindrical body, upper and lower circular plates 13, 14 of the support portion 1 coupled to both ends of the first toe sheath portion 2 respectively, and upper and lower plates 13, 14 of the support portion 1 coupled to both ends of the second toe sheath portion 3 respectively, and the protection pad portion 4 is an arc plate matched with an internal side of a first toe joint of the big toe.

Figure 3:
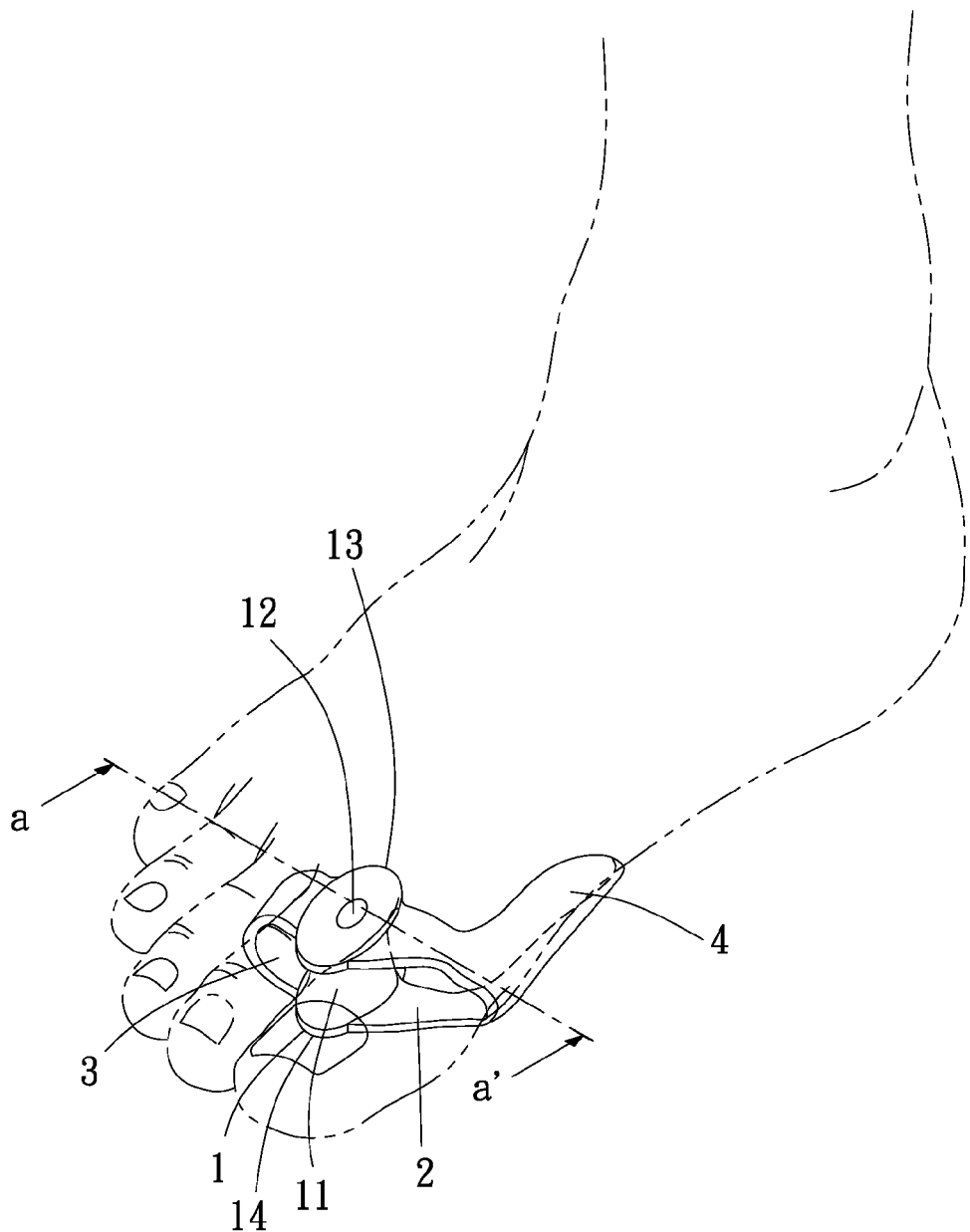
FIG. 3 is a first schematic view of an application in accordance with a preferred embodiment of the present invention.
Figure 4:
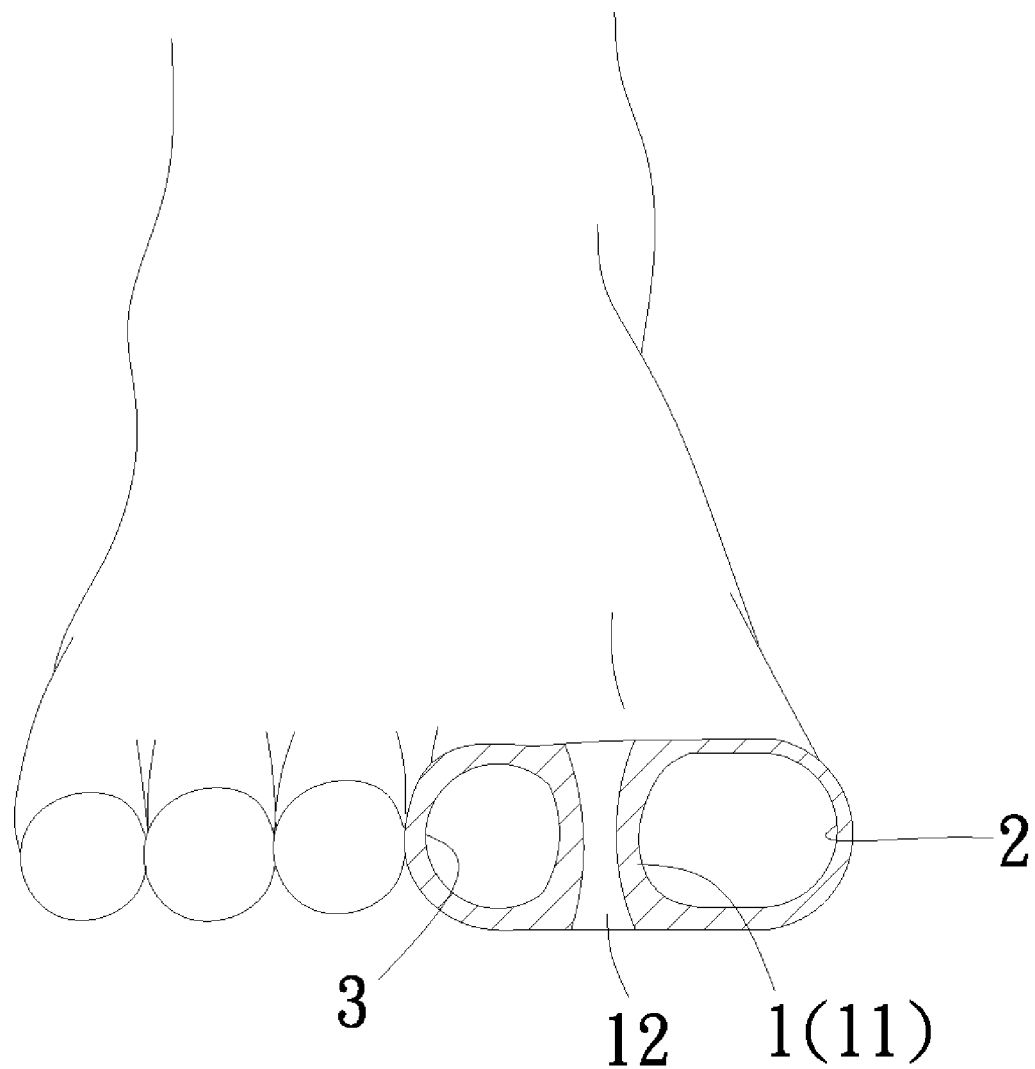
FIG. 4 is a second schematic view of an application in accordance with a preferred embodiment of the present invention.

With reference to FIGS. 3 and 4 for schematic views of an application of the toe extroversion correction device in accordance with the present invention, the first toe sheath portion 2 is sheathed on a big toe, and the second toe sheath portion 3 is sheathed on a second toe, such that the support portion 1 can be clipped between the big toe and the second toe, and the support portion 1 can produce an action force (such as an elastic support and a pushing force) to push away the big toe to correct the extroversion and deformation of the big toe after the device has been worn for a long time, and the big toe will be able to resume its original shape gradually. Particularly, the protection pad portion 4 in form of an arc plate can be attached onto an internal side of the first toe joint of the big toe during the correction period to prevent the protruding portion of the first toe joint of the extroverted big toe from being rubbed with the shoe, and prevent calluses, corns or inflammations.

In summation of the description above, the integrally formed toe extroversion correction device of the invention includes the structural design of the protection pad portion, such that the toe extroversion correction device can be worn onto a big toe and a second toe, and the protection pad portion is attached onto the protruding deformed position of the first toe joint, so as to achieve the effects of correcting the toe extroversion and protecting the internal side of the first toe joint. Obviously, the present invention complies with patent application requirements, and products derived from the present invention fully meet the present market requirements.

While the invention has been described by means of specific embodiments, numerous modifications and variations could be made thereto by those skilled in the art without departing from the scope and spirit of the invention set forth in the claims.

What is claimed is:

1. A toe extroversion correction device, comprising:
a support portion, integrally formed and made of a soft material, the support portion is a cylindrical body having a clamp portion that constitutes a concave arc shape around a middle section of the cylindrical body, the support portion is clipped between a big toe and a second toe;
a first toe sheath portion, disposed on a lateral side of the support portion, the first toe sheath portion has both ends coupled to upper and lower circular plates of the support portion respectively, the first toe sheath portion is sheathed on the big toe;
a second toe sheath portion, disposed on another lateral side of the support portion, the second toe sheath portion has both ends coupled to upper and lower circular plates of the support portion respectively, the second toe sheath portion is sheathed on the second toe; and
a protection pad portion, protruded from a lateral side of the first toe sheath portion, the protection pad portion is an arc-shaped plate matched with an internal side of a first toe joint.

* * * * *